(12) United States Patent
Murphy

(10) Patent No.: US 12,295,585 B2
(45) Date of Patent: May 13, 2025

(54) BALLOON OCCLUSION CATHETER FOR RETROGRADE ANGIOGRAPHY

(71) Applicant: Timothy Patrick Murphy, Providence, RI (US)

(72) Inventor: Timothy Patrick Murphy, Providence, RI (US)

(*) Notice: Subject to any disclaimer, the term of this patent is extended or adjusted under 35 U.S.C. 154(b) by 194 days.

(21) Appl. No.: 17/993,053

(22) Filed: Nov. 23, 2022

(65) Prior Publication Data

US 2023/0233210 A1 Jul. 27, 2023

Related U.S. Application Data

(60) Provisional application No. 63/303,521, filed on Jan. 27, 2022.

(51) Int. Cl.
*A61B 17/12* (2006.01)
*A61M 5/00* (2006.01)
*A61M 25/10* (2013.01)

(52) U.S. Cl.
CPC .... *A61B 17/12136* (2013.01); *A61B 17/1204* (2013.01); *A61M 5/007* (2013.01); *A61M 2025/105* (2013.01); *A61M 2025/1052* (2013.01)

(58) Field of Classification Search
CPC ......... A61B 17/12136; A61B 17/1204; A61M 5/007; A61M 2025/105; A61M 2025/1052; A61M 25/1002; A61M 2025/1059
See application file for complete search history.

(56) References Cited

U.S. PATENT DOCUMENTS

| | | | |
|---|---|---|---|
| 4,638,805 A | 1/1987 | Powell | |
| 4,641,654 A | 2/1987 | Samson | |
| 4,811,737 A | 3/1989 | Rydell | |
| 4,821,722 A | 4/1989 | Miller | |
| 5,078,681 A * | 1/1992 | Kawashima | A61M 25/10 606/198 |
| 5,087,247 A | 2/1992 | Horn | |
| 5,213,576 A | 5/1993 | Abiuso et al. | |
| 5,306,247 A | 4/1994 | Pfenninger | |
| 5,413,571 A * | 5/1995 | Katsaros | A61B 17/0057 606/151 |
| 5,766,151 A * | 6/1998 | Valley | A61M 39/0247 604/103.07 |
| 6,322,577 B1 | 11/2001 | McInnes | |
| 7,873,404 B1 | 1/2011 | Patton | |
| 2002/0122877 A1* | 9/2002 | Harish | A61L 31/16 427/2.24 |
| 2011/0313355 A1 | 12/2011 | Boatman | |
| 2016/0220793 A1 | 8/2016 | Murphy | |
| 2016/0271321 A1 | 9/2016 | Chambers | |
| 2017/0360858 A1* | 12/2017 | Alt | A61F 2/958 |

OTHER PUBLICATIONS

K. Steiner. Pathophysiology of Stenosis Within AV Fistulas and Mechanisms of angioplasty. Endovascular Today 2016;15(6): 28-32.

\* cited by examiner

*Primary Examiner* — Bo Joseph Peng

(57) ABSTRACT

The current invention comprises devices and methods for performance of retrograde angiography, viz, devices and methods of occlusion of a blood vessel and injection of contrast to flow proximal to the direction of blood flow, thereby enabling retrograde clinical angiograms of blood vessels and grafts to be obtained.

1 Claim, 6 Drawing Sheets

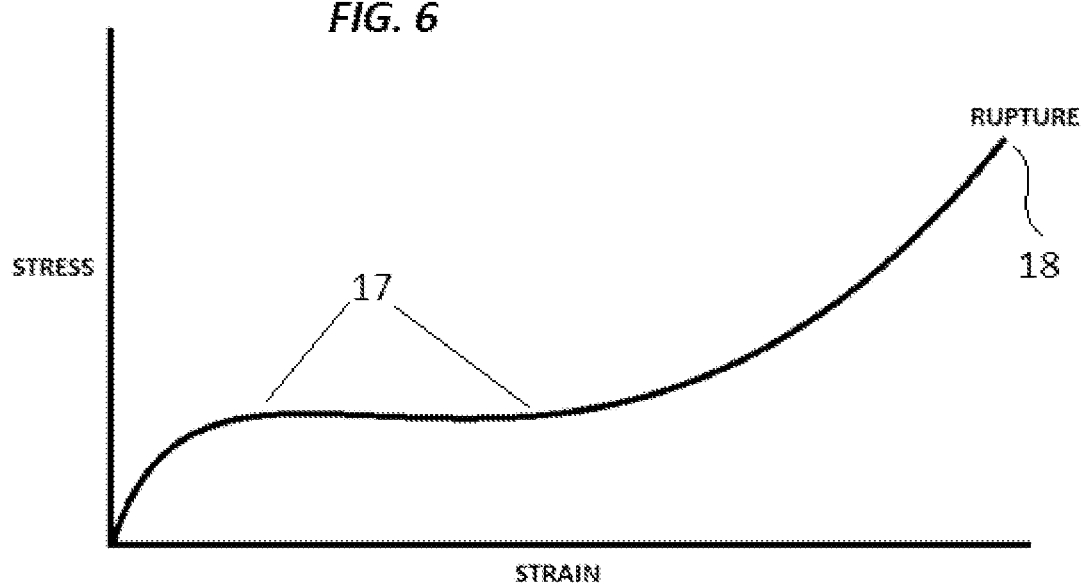

BALLOON OCCLUSION CATHETER FOR RETROGRADE ANGIOGRAPHY

CROSS-REFERENCE TO RELATED APPLICATIONS

This application claims priority under 35 U.S.C. § 119 and 35 U.S.C. § 120 of provisional patent application number 63/303,521, EFS ID 44846798, confirmation number 9885, filed 27 Jan. 2022, entitled "Injectable Occlusion Balloon for Retrograde Angiography", by inventor Timothy Patrick Murphy, docket number 20220126.01, the entirety of which is incorporated herein by reference.

BACKGROUND

U.S. Patents

| Pat. No. | Issue Date | First Inventor |
|---|---|---|
| 4,638,805 | Jan. 27, 1987 | Philip E. Powell |
| 4,641,654 | Feb. 10, 1987 | Wilfred J. Samson |
| 4,811,737 | Mar. 14, 1989 | Mark A. Rydell |
| 4,821,722 | Apr. 18, 1989 | Gary H. Miller |
| 5,087,247 | Feb. 11, 1992 | Joseph B. Horn |
| 5,213,576 | May 25, 1992 | Christopher L. Abiaso |
| 5,306,247 | Apr. 26, 1994 | Susanne Pfenninger |
| 6,322,577 | Nov. 27, 2001 | Peter R. McInnes |
| 7,873,404 | Jan. 18, 2011 | Chris Patton |

U.S. Patent Applications

| U.S. patent application Ser. No. | Publication Date | First Inventor |
|---|---|---|
| 2011/0313355 | Dec. 22, 2011 | Scott E. Boatman |
| 2016/0220793 | Aug. 4, 2016 | Murtagh M. Murphy |
| 2016/0271321 | Sep. 22, 2016 | Christopher Michael Chambers |

Nonpatent Literature

K. Steiner. Pathophysiology of Stenosis Within AV Fistulas and Mechanisms of angioplasty. Endovascular Today 2016; 15 (6): 28-32.

I Bountouris, G Kritikou, N. Degermetzoglou, K. I. Avgerinos. A Review of Percutaneous Transluminal Angioplasty in Hemodialysis Fistula. International Journal of Vascular Medicine 2018; Article ID 1420136, pp. 1-5.

A. Asif, O. Lenz, D. Merrill, et al. Percutaneous management of perianastomotic stenosis in arteriovenous fistulae: results of a prospective study. Kidney Int. 2006; 69:1904-1909.

M. Napoli, R. Prudenzano, F. Russo, A. L. Antonaci, M. Aprile, and E. Buongiorno, "Juxta-anastomotic stenosis of native arteriovenous fistulas: surgical treatment versus percutaneous transluminal angioplasty," The Journal of Vascular Access, vol. 11, no. 4, pp. 346-351, 2010.

B. Long, N. Brichart, P. Lermusiaux et al., "Management of perianastomotic stenosis of direct wrist autogenous radialcephalic arteriovenous accesses for dialysis," Journal of Vascular Surgery, vol. 53, no. 1, pp. 108-114, 2011.

H. Kwon, J. Y. Choi, H. K. Ko et al., "Comparison of surgical and endovascular salvage procedures for juxta-Anastomotic stenosis in autogenous wrist radiocephalic arteriovenous fistula," Annals of Vascular Surgery, vol. 28, no. 8, pp. 1840-1846, 2014.

Angiograms are medical x-ray examinations of tubular structures in the human body, including arteries, veins, arteriovenous fistula, lymphatics, and bile ducts. There are over two million angiograms performed each year in the U.S. In order to perform an angiogram, the operator places a catheter within a tubular structure and injects a radiopaque contrast material, usually iodine-based in liquid form.

In a blood vessel or graft, any radiopaque contrast material will move with the surrounding flowing blood away from the site of injection in an antegrade direction, or in the direction of blood flow. If the operator wants to visualize any part of the blood vessel or graft injected proximal to the site of injection, typically they are required to reposition the catheter to a more proximal location. Alternatively, they could occlude the blood flow downstream from the tip of said catheter for example by external compression using their hand, or an external compression device, such as for example a sphygmomanometer cuff applied around a limb, and any injected contrast will reflux retrograde, against the direction of blood flow.

When kidney function decreases below 10% to 15% the kidneys are no longer able to adequately filter the blood and make sufficient urine, causing certain toxins to build up in the bloodstream along with excess fluid. Hemodialysis is a therapy that filters metabolic waste, removes extra fluid and balances electrolytes. In hemodialysis, blood is removed from the body and filtered through a man-made membrane called a dialyzer and then the filtered blood is returned to the body. To perform hemodialysis there needs to be access created to get the blood from the body to the dialyzer and back to the body. Of the more than 2 million people on dialysis, nearly 500,000 dialyze with either an arteriovenous graft or autologous arterio-venous fistula, the latter of which is preferred by the National Kidney Foundation. Both of these modalities will heretofore be referred to as the AV Access Circuits (AVAC). AVAC's are surgically-created vascular circuits that involve a direct connection between the arterial and venous circulations. The AV fistula is accomplished by anastomosing an artery of the upper or lower arm to a corresponding vein without the use of any foreign material. On the other hand, a graft is created by connecting an artery to a vein with the aid of a tubular conduit, usually made of polytetrafluoroethylene, polyester, nylon, polyethylene terephthalate, or other similar material. In an AV graft stenoses typically occur at the graft-artery and graft-venous anastomoses. In an autologous arterio-venous fistulae, stenoses tend to occur at the surgical arterio-venous anastomosis as well as what is referred to as the juxta-anastomotic segment, which is the segment of vein that lies within the first 4-5 cm of the outflow vein immediately central to the anastomosis, as well as within the native artery just proximal to the anastomosis. These are referred to as inflow lesions of the AVAC. However, stenoses can develop anywhere in the AVAC, secondary to intimal hyperplasia from altered flow dynamics, surgical intervention as well as vessel trauma from cannulation, or catheter insertion, during the dialysis treatment itself. When these intravascular stenoses develop, the velocity of blood flow within the AVAC decreases, which can compromise the quality of the dialysis treatment secondary to reduced clearance of toxins and ultimately lead to complete thrombosis of the AVAC and loss of the access itself. Loss of access can require surgical creation of an entirely new access for dialysis treatment.

Thus, during radiographic examination of AVAC, generally percutaneous access using a needle is gained into a lumen of the AVAC, a guide wire placed through the needle into the blood vessel or graft, the needle removed, and a catheter placed over the guide wire. After removal of the guide wire, imaging of the AVAC can be done by injecting radiopaque contrast and obtaining x-ray images. In order to exam the entire AVAC, contrast must be made to reflux against the direction of blood flow to opacify the arteriovenous or artero-graft anastomosis. This is often done by manual compression over the outflow blood vessel and contrast injection, or occasionally by using a tourniquet such as a sphygmomanometer around the upper arm, central to the injection site, and then injecting contrast forcefully to reflux contrast retrograde, against the direction of blood flow to fill proximal blood vessels or grafts. This maneuver is technically challenging, and can expose the operator to excessive radiation if done manually.

SUMMARY

The devices and methods disclosed herein generally involve an occlusion balloon catheter designed to inject fluids proximal to an occlusion balloon, and using the invention to block outflow of a blood vessel or graft while injecting radiopaque contrast material proximal to that blockage, thereby permitting radiographic contrast to flow retrograde against the normal direction of blood flow. If radiographic contrast is injected at sufficient volume and rate to generate sufficient pressure, contrast will flow proximally against the direction of blood flow, thereby permitting radiographic imaging of the blood vessel or graft proximal to the site of radiographic contrast injection.

A feature of the present invention is the method of using a temporary intraluminal device comprising an element that can be expanded to block blood flow through a blood vessel or graft, such that when contrast is injected proximal to the expanded element it flows retrograde against the normal direction of blood flow, thereby allowing radiographic images to be done of the blood vessel or graft.

BRIEF DESCRIPTION OF THE DRAWINGS

FIG. 6 is an exemplary stress-strain curve plotting stress, or balloon internal pressure, on the y-axis and strain, or balloon diameter on the x-axis.

DETAILED DESCRIPTION

Figure 1:
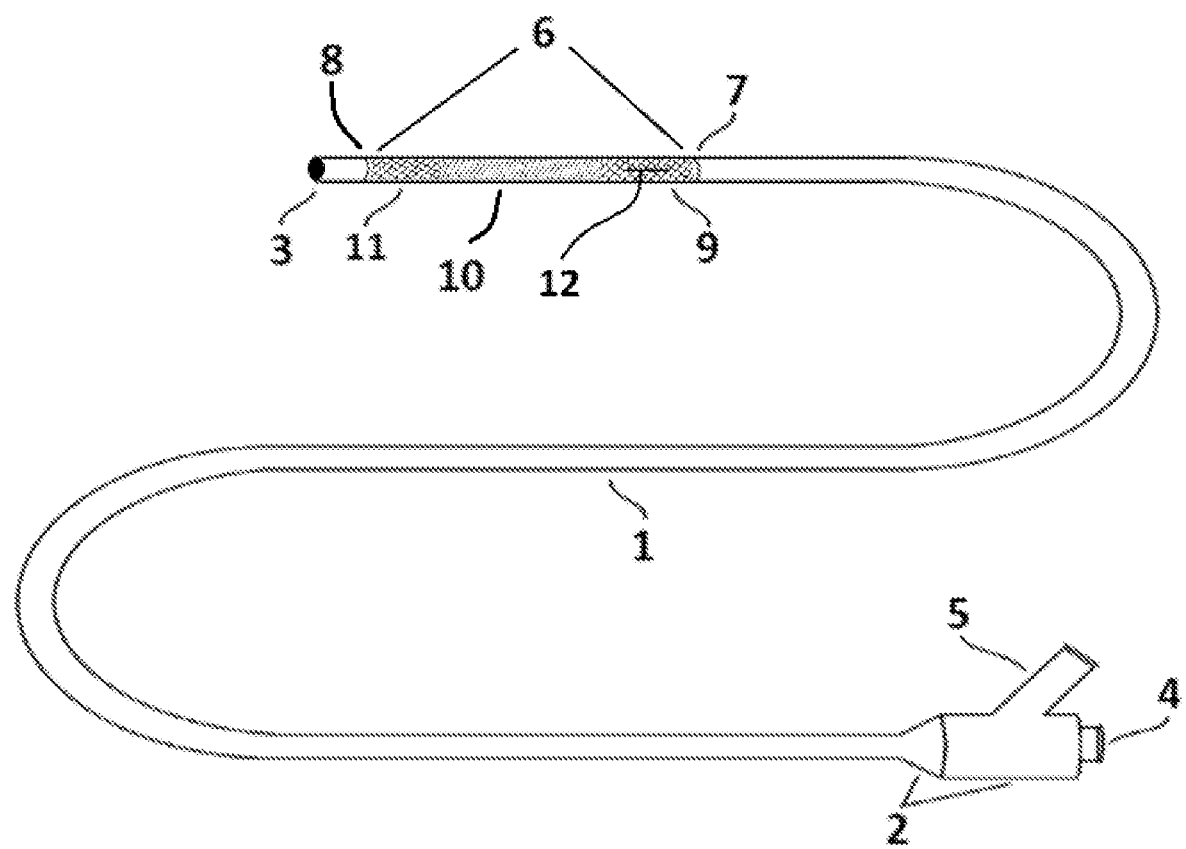
FIG. 1 is a surface view that depicts a view of an embodiment of the invention, in this case an occlusion balloon catheter with at least one aperture in an expansile balloon proximal cone, shown with said occlusion balloon collapsed.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Devices and related methods are disclosed that generally involve the use of the invention during angiography whereby outflow from a blood vessel or graft is blocked so that contrast injected through the device flows retrograde against the typical direction of blood flow. In a preferred embodiment, the pressure required to fully inflate said angioplasty balloon is less than the pressure required to open an aperture in the angioplasty balloon that releases injection fluids, so that when fluids are injected into a balloon inflation lumen a balloon is inflated substantially to cause a blockage in a blood vessel or graft and remains inflated when an aperture opens and injected fluids are expelled from the catheter. By way of example, said pressure ranges required to open said aperture could be between 1 and 20 atmospheres, or more specifically between 1 and 3 atmospheres, or between 3 and 6 atmospheres, or 6 and 9 atmospheres, or 9 to 12 atmospheres, or 12 to 15 atmospheres, or 15 to 20 atmospheres, as determined by routine experimentation familiar to those experienced in the art. Moreover, since the purpose of the aperture is to release radiopaque fluids at sufficient rate to perform a clinical angiogram, the cross-sectional area of said aperture would have to be sufficient to allow fluids to be injected at a satisfactory rate such that contrast is dense enough in said blood vessel or graft to be angiographically sufficient such that a clinical angiogram is obtained by the user when fluid is injected manually by an operator using a syringe, or by a mechanical injector, using inflation pressures between 1 and 30 atmospheres. Said cross-sectional area could be for example 0.05-6 $mm^2$, or 0.05-0.2 $mm^2$, or 0.2-0.4 $mm^2$, or 0.4-0.8 $mm^2$, or 0.08-1.5 $mm^2$, or 1.5-3 $mm^2$, or 3-6 $mm^2$. It would be apparent to those familiar with the art that the cross-sectional area of said aperture could be comprised by more than one aperture. Radiopaque fluids injected to obtain angiograms generally used iodine-containing solutions, such solutions being in the range of 10% to 76% iodine-containing molecule by w/v, or for example containing 47 mg/ml of iodine, or for example 360 mg/ml of iodine. In order to obtain a clinical adequate angiogram, injection rates in the range of 0.1 ml/second to 40 ml/second of said radiopaque fluids are generally required, depending on the location of the blood vessel or graft, and should be achieved with between 3 and 30 atmospheres of injection pressure. For example, a flow rate of between 0.1 ml/second and 1 ml/second of said radiopaque fluids generally would be sufficient for imaging of a distal small blood vessel or graft, whereas a flow rate between 0.5 ml/second and 3 ml/second would be substantially adequate for a more proximal small blood vessel or graft; injection of radiopaque fluids at a rate of 1 ml/second to 5 ml/second would be substantially adequate for a more proximal medium sized blood vessel or graft; injection of 5 ml/second to 20 ml/second would generally be suitable for angiography of a large proximal blood vessel or graft.

FIG. 1 depicts an exemplary preferred embodiment of the invention, in this case a lateral surface view of an occlusion balloon catheter depicted in a collapsed balloon configuration. Said occlusion balloon catheter comprises a tubular element 1 that extends from a proximal hub 2 to a distal end hole 3 at said tubular element's distal tip end, said proximal hub 2 further comprising a proximal end hole 4 of a first lumen for passing a guide wire there through, and said proximal hub 2 further comprising a side arm hole 5 of a second lumen in fluid communication with an interior of an expansile balloon 6 as a means of inflation of said expansile balloon 6 securely attached to said tubular element 1 at said expansile balloon's proximal end 7 and further at said expansile balloon's distal 8 end, said expansile balloon 6 further comprising at least a proximal section 9, at least a middle section 10, and at least a distal section 11, said expansile balloon further comprising at least one aperture 12 in said expansile balloon proximal to said middle section 10, said aperture 12 being substantially closed when insufficiently pressurized by injection of fluids into said side arm hole 5 of said second lumen, and said aperture 12 further being substantially open when pressurized by injection of fluids into said sidearm of said second lumen when a threshold pressure is achieved, said threshold pressure being greater than that which is required to inflate said expansile balloon 6 to a diameter to substantially occlude flow in a blood vessel or graft.

In an exemplary embodiment of the invention depicted in FIG. 1, said proximal section 9 (crossed hash marks) and said distal section 11 (crossed hash marks) of said expansile balloon comprise a lower elasticity than said middle section 10 (single hash marks), such that injection of fluids or gases through said second lumen achieves a first an inflation in said middle section 10 at a first pressure, and then as said fluids or gases continue to be injected, progressive expansion of a wall of said expansile balloon 6 results in increasing pressure within an interior of said expansile balloon 6 until a second pressure is achieved, resulting in inflation of said proximal section 9 and said distal section 11, causing said injected fluids or gases to flow into said proximal section 9 and escape from said aperture 12 and extending proximally to said expansile balloon 6 in a vascular system. Such an occlusion balloon 6 may inflate to diameters between 3 and 12 mm, and could be between 2 and 20 cm long, and be mounted on a tubular element 1 between 10 and 170 cm long. Further, a first pressure threshold required to expand a middle section 10 could be between 1 and 20 atmospheres, and a second pressure threshold required to expand a proximal section 9 could be between 1 and 20 atmospheres. The pressure gradient, defined as the difference between said first pressure threshold and said second pressure threshold, could be between 1 and 20 atmospheres, with said second pressure being greater than said first pressure by between 1 and 20 atmospheres. Occlusion balloon catheters may be "over the wire", typically with at least a guide wire lumen and at least a balloon inflation lumen, or may be "rapid exchange", comprising only a balloon inflation lumen throughout its length. Occlusion balloon catheters can also be configured with an integral guide wire or a tapered tip if intended to be used alone without a guide wire, such as for example in the case of a single lumen occlusion balloon catheter.

Those familiar with the art will appreciate that a constraining apparatus that prevents inflation of said expansile balloon 6 after it reaches a particular diameter would cause a fluid pressure within said expansile balloon 6 to rapidly rise once said particular diameter were achieved could also be used to actuate a proximal section 9 or distal section 11 to inflate, said pressurized fluids then escaping from said aperture 12.

Figure 2:
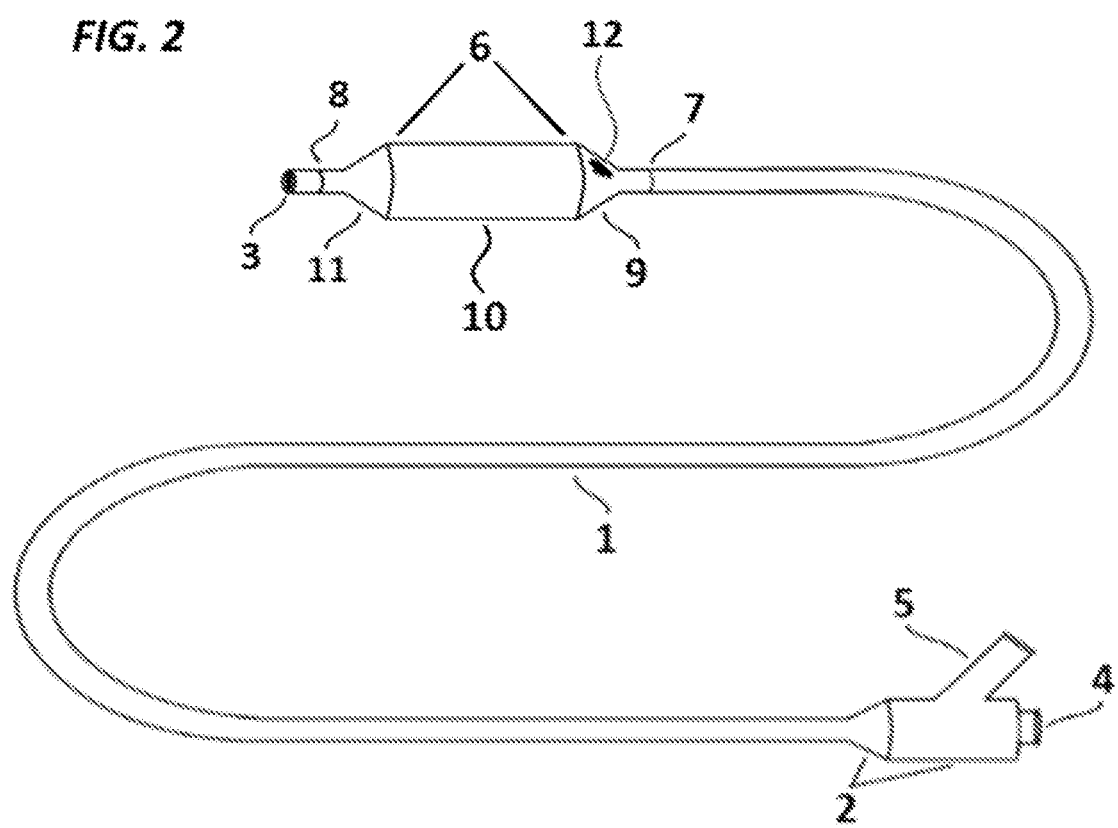
FIG. 2 is another surface view that depicts another embodiment of the invention as in FIG. 1, in this case an occlusion balloon catheter with at least one aperture in an expansile balloon proximal cone, shown with said occlusion balloon inflated.

FIG. 2 depicts another embodiment of the invention as in FIG. 1, in this case a lateral surface view of an occlusion balloon catheter depicted in an expanded balloon configuration. In this illustration of an embodiment, the balloon has expanded such that its internal pressure is greater than a threshold pressure required to expand a proximal section 9. This illustration further shows opening of an aperture in a proximal section 9 such that fluid injected into an interior of said expansile balloon 6 is able to exit an aperture 12 in said proximal section 9. It will be appreciated by those familiar with the art that an opening of said second lumen (not shown) in an interior of said expansile balloon 6 used for injection of fluids or gases to effect inflation of said expansile balloon would generally be disposed toward a distal end of said expansile balloon, so that inflation of said balloon must occur before any fluid or gas reaches an interior of said proximal section 9, from where it could leak out of said aperture 12 prematurely, that is, before said expansile balloon 6 is inflated enough to effectuate occlusion of a blood vessel or graft.

Those familiar with the art will readily recognize embodiments of the invention wherein an aperture 12 on said proximal section 9 is in an "always open" configuration, a "partially open" configuration, or a "closed configuration" before pressure is achieved sufficient to expand said proximal section 9. Moreover, said aperture 12 could be configured in an overlapping flap configuration.

Thus, upon pressurization of a second lumen with fluid or gas, the disclosed invention works dynamically to first inflate an expansile balloon 6 without generally any substantial injected fluid or gas exiting an aperture 12 from a proximal section 9, but when injection of fluids into said second lumen achieves a threshold pressure said proximal section 9 expands, moving its walls away from apposition to said tubular element, thereby permitting injected fluids access said aperture 12 and exit from said expansile balloon 6. In this way, occlusion angiography can be performed in a retrograde manner. That is, for example, contrast containing fluids or gases injected into said second lumen will inflate said expansile balloon 6 to achieve occlusion of a blood vessel or graft, and further injection of contrast containing fluids or gases will expand said proximal section 9 with a higher elastic modulus (lower elasticity) than said middle section 10 and then exit from said aperture 12, passing proximally to opacify a blood vessel or graft proximal to said expansile balloon 6, allowing angiography to be performed in a proximal direction against the direction of blood flow.

Moreover, it is apparent to those familiar with the art that the same result disclosed in the invention would be achieved in an embodiment in which the expansion of the balloon and release of injected radiopaque fluids from an always-open proximally disposed at least an aperture both occur substantially simultaneously, since, depending on the cumulative cross-sectional area of the at least an aperture, a balance can be achieved between the amount of injected fluid that is lost through the aperture and the amount that expands the expansile balloon that the same endpoint is achieved, viz, expansion of the expansile balloon to substantially comprise a blockage in a blood vessel or graft and exit of radiopaque fluids from a proximal aperture into a blood vessel or graft at a sufficient rate to obtain a clinical radiographic angiogram in a retrograde fashion of proximal blood vessels or grafts.

Those familiar with the art will further appreciate that said aperture in said proximal collar may comprise a defect in the weld between the proximal collar and said tubular element 1 comprising part or the entirety of said weld. Moreover, an exit port for injected fluids proximal to an expansile balloon could be situated on said tubular element itself.

It will also be apparent that as an elastic balloon expands any aperture will expand as well, resulting in more injected fluid exiting the balloon the larger it gets.

Figure 3:
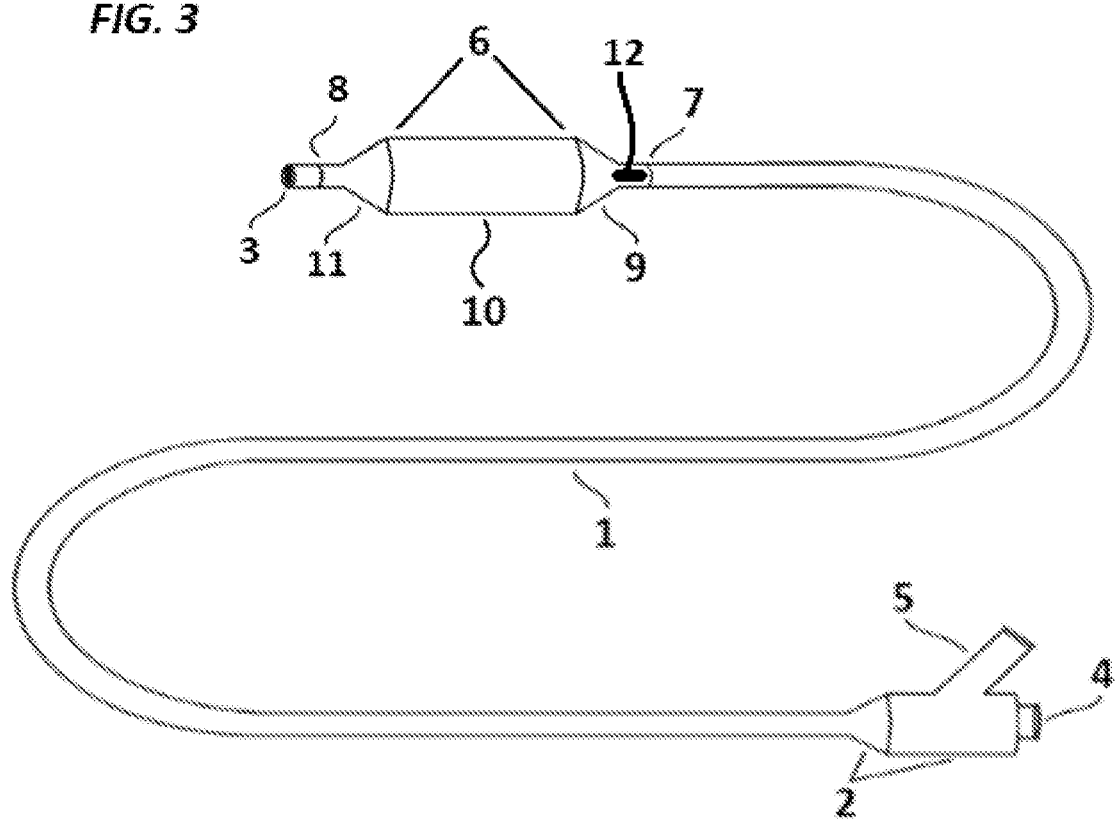
FIG. 3 is another surface view that depicts an embodiment of the invention with an aperture on a proximal collar of an expansile balloon.

FIG. 3 shows an exemplary embodiment of the invention in which an aperture 12 is located on a proximal balloon collar, or that portion of an expansile balloon which is annealed or welded to a catheter. In this example, the aperture is located on a proximal cuff in an area that is not securely bonded to an underlying catheter, such that when a threshold inflation pressure is achieved in an interior of an expansile balloon, said cuff can be sufficiently lifted off of said catheter to permit flow of fluids therein, thereby allowing said fluids to exit said aperture 12 into a blood vessel or graft proximal to said expansile balloon.

Figure 4:
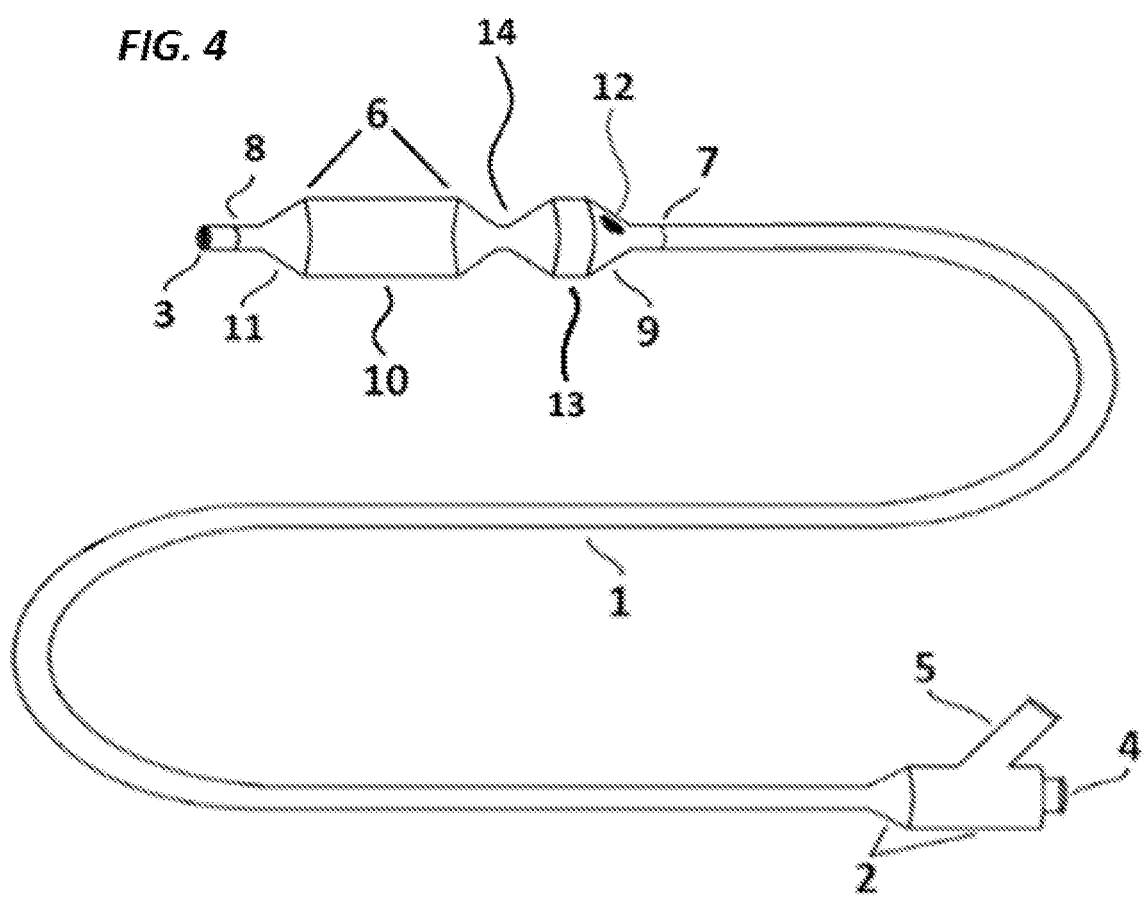
FIG. 4 is a surface view of another embodiment of the invention, in this example an occlusion double balloon catheter with at least an aperture in a proximal expansile balloon, shown with said occlusion balloons both inflated.

Those familiar with the art will also appreciate that another embodiment of the invention is a double expansile balloon configuration, an example of which is shown in an expanded balloon configuration in FIG. 4. In such an exemplary embodiment, a first expansile balloon 6 is more distally disposed than a second expansile balloon 13, said first expansile balloon 6 being in communication with said second expansile balloon 13 through an intervening choke segment 14, said choke segment 14 having a higher elastic modulus (lower elasticity) than said first expansile balloon 6 and not allowing fluids injected into an interior of said first expansile balloon 6 to access an interior of said second expansile balloon 13 until a threshold pressure is achieved, said threshold pressure exceeding a pressure required to substantially inflate said first expansile balloon 6, said second expansile balloon further comprising an aperture 12 for exit of said injected fluids from said interior of said second expansile balloon into a blood vessel or graft proximal to said expansile balloon 6. Those familiar with the art will appreciate that sequential inflation of an expansile balloon 6 followed by expulsion of fluid from an aperture 12 can be facilitated by having three moduli of elasticity, such that an expansile balloon has a first modulus of elasticity, a choke section 14 has a second higher modulus of elasticity, and a second expansile balloon 13 has a third modulus of elasticity, which may be between the first and second moduli of elasticity or similar to a first modulus of elasticity. It will be appreciated by those familiar with the art that reducing elasticity (higher elastic modulus) in any section of an expansile balloon can be achieved by providing more material in said section, thickening the wall of said section, or constraining said section's expansion by other mechanical means, such as external wrapping of said section with additional layers of circumferential material, whereas increasing elasticity (lower elastic modulus) can be achieve by thinning wall material. Passage of fluid or gas between a first expansile balloon 6 and a second expansile balloon 13 could also be facilitated using a valve situated between them. Such a double balloon could be comprised of two separate balloons further comprising a communication between said interiors of said balloons, or a single balloon with a dumbbell or hourglass configuration, viz, comprising a substantial waist between two expansile segments.

Figure 5:
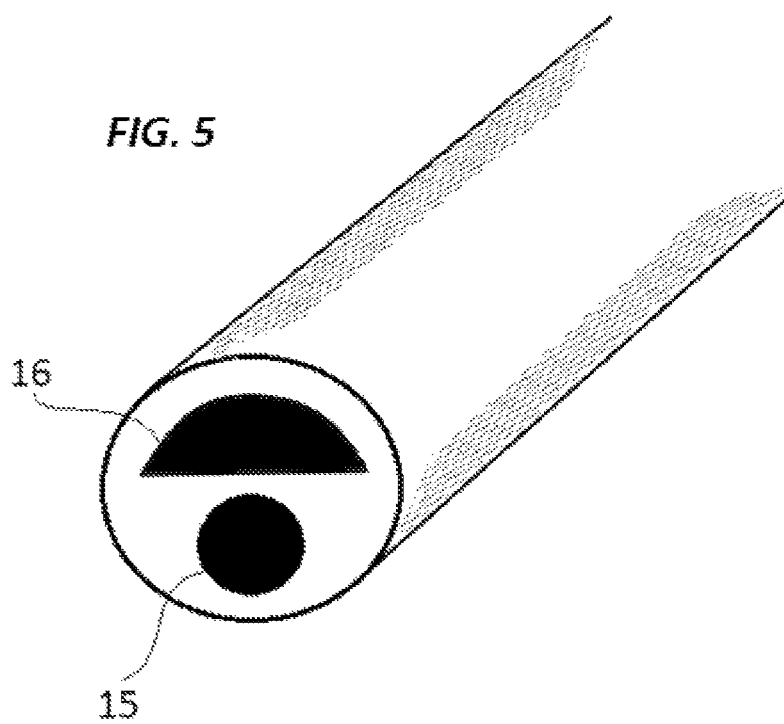
FIG. 5 is a cross-sectional view of an exemplary embodiment of a tubular element of the invention.

FIG. 5 is an exemplary embodiment of a cross-section of a biluminal tubular element that comprises a catheter shaft, in this example showing a circular first lumen 15 for passage of a guidewire there through and a demi-lune cross-sectional shape of a second lumen 16 as a means for injection of pressurized gas or fluid to inflate an expansile balloon 6 and to aspirate said gas or fluid to deflate said expansile balloon 6. Those familiar with the art will recognize that many alternative cross-sectional lumen shapes are possible within the limitations of the disclosed invention.

Those familiar with the art will be aware that expansile balloons of a relatively lower elastic modulus, such as those made of visco-elastic rubbers or polyvinyl chloride, have a triphasic stress-strain response, having an early peak in their pressure-diameter curves, such that the initial inflation to a smaller first diameter requires more internal pressure than incremental inflation from said first diameter to a larger second diameter, said incremental inflation occurring with little or no increase in internal pressure, but with further inflation a diameter is reached where compliance is reduced and pressure increases again until a critical diameter is exceeded and the expansile balloon ruptures (FIG. 6). As can be seen from FIG. 6, initial application of inflation pressure does not change a balloon diameter much, but once a threshold pressure is achieved there is a long plateau 17, or range where increases in pressure result in little change in balloon diameter. If internal pressure continues to be increased, eventually a limit is reached and internal pressure begins to rise and the diameter continues to expand until the balloon ruptures 18. This can poses technical problem because if a proximal section 9 and distal section 11 are less compliant, for example by being more thick walled, than a middle section 10, said middle section 10 could inflate to rupture before adequate pressure is sufficient to inflate said proximal section 9 and said distal section 10 when otherwise unconstrained. There are two ways to avoid this. The first is to ensure that the stress-strain curves of a middle section 10 is tuned to the requirements of the stress-strain curve of the proximal section 9, viz, a proximal section 9 inflates only after the middle section 10 has achieved sufficient diameter to occlude a blood vessel or graft but before said middle section 10 experiences such high pressures that it ruptures. In that case, the apparatus would work as described even when unconstrained. However, for practical reasons the stress-strain curves don't have to be matched so closely, because the pressure dynamics would be different when used in a blood vessel or graft. Namely, when used in a blood vessel or graft, said middle section 10 will be constrained by a wall of said blood vessel or graft, and therefore if said middle section 10 is more compliant than a proximal section 9 it would expand first until it is constrained by the wall of a blood vessel or graft, at which point expansion of a middle section 10 would cease. Having lower compliance in a proximal section 9 and distal section 11 would prevent elongation of said middle section 10 wall. Once further expansion of said middle section 10 is constrained by the wall of a blood vessel or graft and it can't elongate, continued injection of fluid or gas will increase the pressure within the interior of the balloon, since it is not expanding it will not rupture, but rather will contain the pressure until a critical threshold required for inflation of proximal section 9 and distal section 11 is achieved, whereupon said proximal section 9 will inflate and said fluid or gas will access said aperture 12 in said proximal section 9 and exit the expansile balloon 6 and into a blood vessel or graft proximal to said expansile balloon.

Another embodiment of the invention comprises a single lumen catheter with at least an expansile balloon that when expanded causes an obstruction of a blood vessel or graft, further comprising at least an aperture disposed proximal to said obstruction, said single lumen being a means of inflation of said expansile balloon and further a means of injection of fluids that exit said aperture 12 and into a blood vessel or graft. Those familiar with the art will appreciate that such an embodiment may comprise a single-lumen tubular element with an occluded distal lumen or an integral guide wire tip, said single lumen serving balloon inflation and injection of fluids or gases into a blood vessel or graft.

Any of an expansile balloon 6, proximal section 9, distal section 11, or choke section 14 can be made of elastic materials such as for example visco-elastic rubber or polyvinyl chloride, or relatively less elastic materials such as polyester or polyamides, or similar polymers.

INCORPORATION BY REFERENCE

References and citations to other documents, such as patents, patent applications, provisional patent applications, patent publications, journals, books, papers, web content, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

CONCLUSIONS

The reader will appreciate that the invention disclosed of a balloon occlusion catheter for retrograde angiography offers many advantages in permitting radiographic visualization of blood vessels or grafts proximal to the site of contrast entry into the vascular system, contrary to the normal direction of flow within that vascular system. This is particularly applicable in the diagnostic evaluation of dialysis grafts and dialysis fistulae, a routine part of which requires retrograde opacification of an arteri-venous anastomosis created by a surgeon. Surgical arteriovenous fistulae are known to stenose or narrow, and such stenosis can reduce blood flow and render a fistula useless for dialysis.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. A method of performing a retrograde angiography comprising in combination,
    a. insertion of a balloon occlusion catheter into a blood vessel, said balloon occlusion catheter comprising a tubular element with at least an expansile member disposed toward a distal tip end of said catheter, said expansile member comprising an inner lumen, said expansile member further comprising at least an aperture between said inner lumen and an exterior, said catheter comprising at least a lumen for injection of fluids into said inner lumen for inflation of said expansile member sufficient to comprise a blockage in a blood vessel or graft, said aperture located such that fluid that exits from said inner lumen flows proximal to said blockage in said blood vessel or graft along a longitudinal axis of said balloon occlusion catheter retrograde to the direction of blood flow;
    b. injection of radiopaque fluids into said lumen to expand said expansile member so that said expansile member comprises a blockage of a blood flow in said blood vessel;
    c. further injection of said radiopaque fluids into said lumen, thereby releasing said radiopaque fluids from said aperture proximal to said blockage in said blood vessel retrograde to the direction of blood flow;
    d. obtaining radiographic images of said blood vessel or graft proximal to said expansile member.

* * * * *